United States Patent
Deno et al.

(10) Patent No.: US 11,553,867 B2
(45) Date of Patent: Jan. 17, 2023

(54) SYSTEMS AND METHODS FOR DISPLAYING EP MAPS USING CONFIDENCE METRICS

(71) Applicant: St. Jude Medical, Cardiology Division, Inc., St. Paul, MN (US)

(72) Inventors: Don Curtis Deno, Andover, MN (US); Emma K. Davis, Saint Paul, MN (US); Thomas P. Hartley, St. Paul, MN (US); Dennis J. Morgan, Crystal, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 133 days.

(21) Appl. No.: 16/803,578

(22) Filed: Feb. 27, 2020

(65) Prior Publication Data

US 2020/0275851 A1 Sep. 3, 2020

Related U.S. Application Data

(60) Provisional application No. 62/811,917, filed on Feb. 28, 2019.

(51) Int. Cl.
*G06T 17/00* (2006.01)
*A61B 5/339* (2021.01)
(Continued)

(52) U.S. Cl.
CPC .......... *A61B 5/339* (2021.01); *G06F 3/04847* (2013.01); *G06T 17/00* (2013.01); *A61B 5/283* (2021.01); *G06T 2210/41* (2013.01)

(58) Field of Classification Search
CPC ....... A61B 5/339; A61B 5/283; A61B 5/7425; G06F 3/04847; G06T 17/00; G06T 2210/41
See application file for complete search history.

(56) References Cited

U.S. PATENT DOCUMENTS

| 5,579,764 A | 12/1996 | Goldreyer |
| 6,298,255 B1 | 10/2001 | Cordero et al. |

(Continued)

FOREIGN PATENT DOCUMENTS

| EP | 1808124 A2 | 7/2007 |
| EP | 2826418 A1 | 1/2015 |

(Continued)

OTHER PUBLICATIONS

ArcMap ("ArcMap 10.2 Time Enabled Datasets and Time Slider", published by Harvard CGA on YouTube as of Apr. 24, 2014, at https://www.youtube.com/watch?v=cFHc-cmoLIQ) (Year: 2014).*

(Continued)

*Primary Examiner* — William A Beutel
(74) *Attorney, Agent, or Firm* — Armstrong Teasdale LLP

(57) ABSTRACT

Systems and methods for generating and displaying an electrophysiology (EP) map are provided. A system includes a device including at least one sensor configured to collect a set of location data points, and a computer-based model construction system coupled to the device and configured to generate a geometry surface model from the set of location data points, associate an EP parameter with each of a plurality of points on the geometry surface model to generate an EP map, calculate a confidence metric for the EP parameter associated with each point, and display the EP map based on the calculated confidence metrics.

20 Claims, 8 Drawing Sheets

(51) Int. Cl.
*G06F 3/04847* (2022.01)
*A61B 5/283* (2021.01)

(56) References Cited

U.S. PATENT DOCUMENTS

| | | | |
|---|---|---|---|
| 6,301,496 | B1 | 10/2001 | Reisfeld |
| 9,186,081 | B2 | 11/2015 | Afonso et al. |
| 9,277,872 | B2 | 3/2016 | Harlev et al. |
| 10,485,438 | B2 | 11/2019 | Narayan et al. |
| 2002/0165448 | A1 | 11/2002 | Ben-Haim et al. |
| 2007/0073179 | A1 | 3/2007 | Afonso et al. |
| 2009/0069704 | A1 | 3/2009 | MacAdam et al. |
| 2009/0112106 | A1 | 4/2009 | Zhang |
| 2009/0124915 | A1 | 5/2009 | MacAdam |
| 2009/0147005 | A1* | 6/2009 | Kincaid ............... G06T 11/206 345/440 |
| 2009/0275827 | A1 | 11/2009 | Aiken et al. |
| 2009/0281439 | A1 | 11/2009 | Harlev et al. |
| 2009/0324035 | A1* | 12/2009 | Wengler ............... G06K 9/6292 382/128 |
| 2010/0204552 | A1 | 8/2010 | Yamamoto et al. |
| 2012/0144325 | A1* | 6/2012 | Mital .................... G06T 11/206 715/763 |
| 2016/0078657 | A1* | 3/2016 | McCord ............... G06T 19/006 345/440 |
| 2017/0364090 | A1* | 12/2017 | Grufman ................. G01S 19/13 |
| 2018/0174314 | A1* | 6/2018 | Bippus .................. G06T 11/006 |
| 2018/0260951 | A1* | 9/2018 | Yang ..................... G06N 3/084 |

FOREIGN PATENT DOCUMENTS

| | | |
|---|---|---|
| WO | 2011127211 A3 | 10/2011 |
| WO | 2016134264 A1 | 8/2016 |
| WO | 2018148532 A1 | 8/2018 |

OTHER PUBLICATIONS

International Search Report for International Patent Application No. PCT/US2020/020102, dated May 25, 2020, 5 pages.

* cited by examiner

SYSTEMS AND METHODS FOR DISPLAYING EP MAPS USING CONFIDENCE METRICS

CROSS REFERENCE TO RELATED APPLICATIONS

This application claims priority to provisional application Ser. No. 62/811,917, filed Feb. 28, 2019, which is incorporated herein in its entirety.

FIELD OF THE DISCLOSURE

The present disclosure relates generally to generating electrophysiology maps for anatomical structures. In particular, the present disclosure relates to calculating confidence metrics for electrophysiology parameters and displaying electrophysiology maps based on the calculated confidence metrics.

BACKGROUND

The human heart muscle routinely experiences electrical currents traversing its many surfaces and ventricles, including the endocardial surfaces. Just prior to each heart contraction, the heart muscle is said to "depolarize" and "repolarize," as electrical currents spread across the heart and throughout the body. In a healthy heart, the surfaces and ventricles of the heart will experience an orderly progression of a depolarization wave. In an unhealthy heart, such as those experiencing atrial arrhythmia, including for example, ectopic atrial tachycardia, atrial fibrillation, and atrial flutter, the progression of the depolarization wave may not be so orderly. Arrhythmias may persist as a result of scar tissue or other obstacles to rapid and uniform depolarization. These obstacles may cause depolarization waves to repeat a circuit around some part of the heart. Atrial arrhythmia can create a variety of dangerous conditions, including irregular heart rates, loss of synchronous atrioventricular contractions, and stasis of blood flow, all of which can lead to a variety of ailments and even death.

Medical devices, such as, for example, mapping, electroporation, and/or electrophysiology catheters, are used in a variety of diagnostic and/or therapeutic medical procedures to treat such heart arrhythmias. Typically in a procedure, a catheter is manipulated through a patient's vasculature to a patient's heart, for example, and carries one or more electrodes that may be used for mapping, ablation, diagnosis, and/or to perform other functions.

As three-dimensional mapping techniques incorporate increasingly sophisticated interpretations of physiology, there may be uncertainties in acquired electrophysiology parameters used to generate electrophysiology maps. To aid physicians, it would be useful to indicate a confidence metric associated with such parameters (i.e., a metric indicating how likely it is that the associated electrophysiology measurement is reliable). However, generating such a metric may be challenging, particularly when dealing with in vivo data that does not have a known correct value.

BRIEF SUMMARY OF THE DISCLOSURE

In one embodiment, the present disclosure is directed to a system for generating and displaying an electrophysiology (EP) map. The system includes a device including at least one sensor configured to collect a set of location data points, and a computer-based model construction system coupled to the device and configured to generate a geometry surface model from the set of location data points, associate an EP parameter with each of a plurality of points on the geometry surface model to generate an EP map, calculate a confidence metric for the EP parameter associated with each point, and display the EP map based on the calculated confidence metrics.

In another embodiment, the present disclosure is directed to a computer-implemented method for generating and displaying an electrophysiology (EP) map. The method includes generating a geometry surface model from a set of location data points, associating an EP parameter with each of a plurality of points on the geometry surface model to generate an EP map, calculating a confidence metric for the EP parameter associated with each point, and displaying the EP map based on the calculated confidence metrics.

In yet another embodiment, the present disclosure is directed to a processing apparatus for generating and displaying an electrophysiology (EP) map. The processing apparatus is configured to generate a geometry surface model from a set of location data points, associate an EP parameter with each of a plurality of points on the geometry surface model to generate an EP map, calculate a confidence metric for the EP parameter associated with each point, and display the EP map based on the calculated confidence metrics.

The foregoing and other aspects, features, details, utilities and advantages of the present disclosure will be apparent from reading the following description and claims, and from reviewing the accompanying drawings.

DETAILED DESCRIPTION OF THE DISCLOSURE

The present disclosure provides systems and methods for displaying an electrophysiology (EP) map are provided. Initially, a plurality of location data points are collected, and a geometry surface model is generated from the set of location data points. To generate an EP map, an EP parameter is associated with each of a plurality of points on the geometry surface model. A confidence metric is calculated for each EP parameter, and the EP map is displayed based on the calculated confidence metrics.

Figure 1:
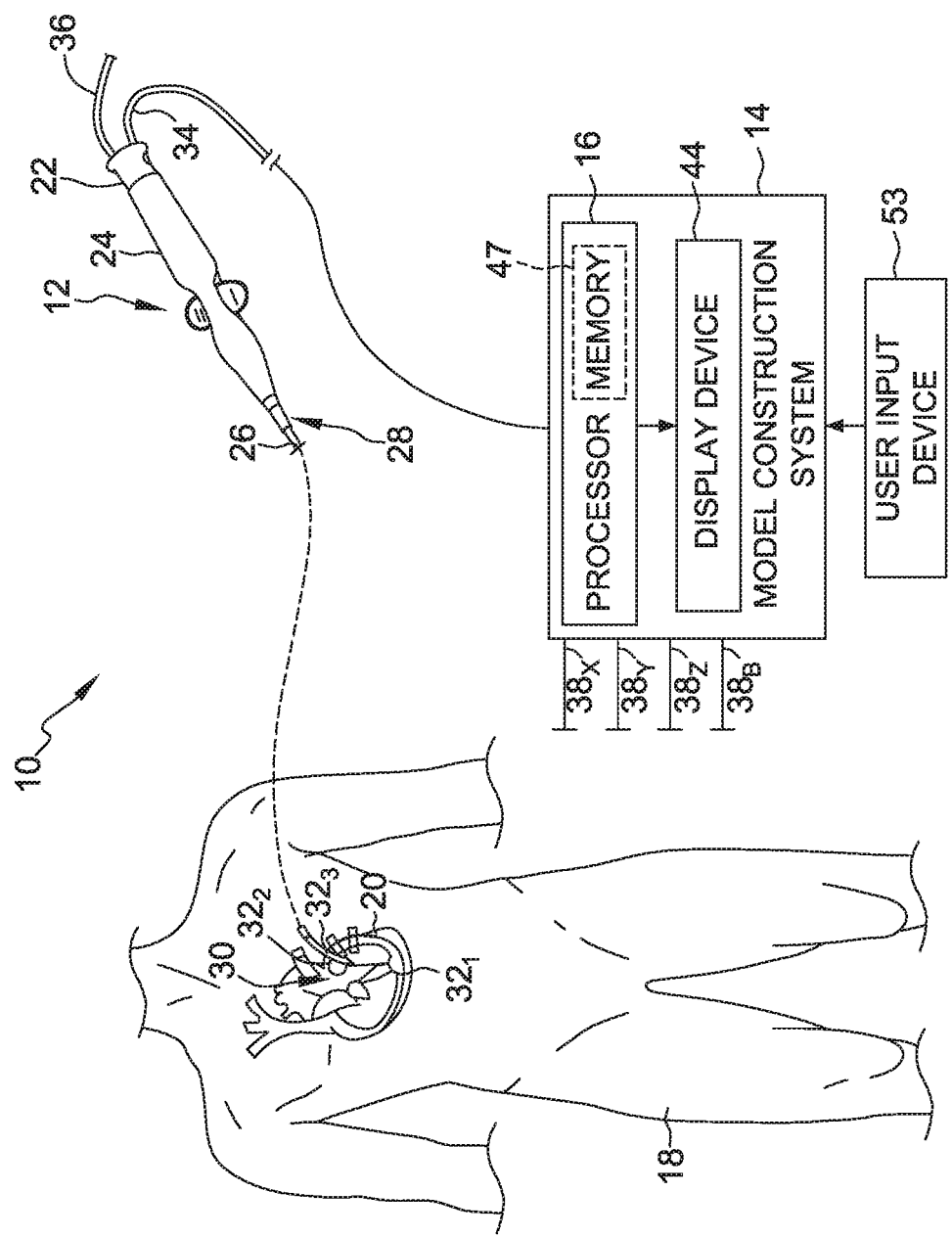
FIG. 1 is a diagrammatic view of a system for generating a multi-dimensional surface model of a geometric structure according to one embodiment.

Referring now to the drawings wherein like reference numerals are used to identify identical components in the various views, FIG. 1 illustrates one exemplary embodiment of a system 10 for generating a multi-dimensional surface model of one or more geometric structures. As will be described below, in this embodiment, the model generated by system 10 is a three-dimensional model. It will be appreciated, however, that while the generation of a three-dimensional model is described below, the present disclosure is not meant to be so limited. Rather, in other embodiments, system 10 may be configured to generate multi-dimensional models other than in three-dimensions, and such embodiments remain within the spirit and scope of the present disclosure.

It should be further noted that while the following description focuses primarily on the use of system 10 in the generation of models of anatomic structures, and cardiac structures in particular, the present disclosure is not meant to be so limited. Rather, system 10, and the methods and techniques used thereby, may be applied to the generation of three-dimensional models of any number of geometric structures, including anatomic structures other than cardiac structures. However, for purposes of illustration and ease of description, the description below will be limited to the use of system 10 in the generation of three-dimensional models of cardiac structures.

With continued reference to FIG. 1, in this embodiment, the system 10 includes, among other components, a medical device and a model construction system 14. In this embodiment, the medical device is a catheter 12, and model construction system 14 includes, in part, a processing apparatus 16. Processing apparatus 16 may take the form of an electronic control unit, for example, that is configured to construct a three-dimensional model of structures within the heart using data collected by catheter 12

As illustrated in FIG. 1, catheter 12 is configured to be inserted into a patient's body 18, and more particularly, into the patient's heart 20. Catheter 12 may include a cable connector or interface 22, a handle 24, a shaft 26 having a proximal end 28 and a distal end 30 (as used herein, "proximal" refers to a direction toward the portion of the catheter 12 near the clinician, and "distal" refers to a direction away from the clinician and (generally) inside the body of a patient), and one or more sensors 32 (e.g., $32_1$, $32_2$, $32_3$) mounted in or on shaft 26 of catheter 12. In this embodiment, sensors 32 are disposed at or near distal end 30 of shaft 26. Catheter 12 may further include other conventional components such as, for example and without limitation, a temperature sensor, additional sensors or electrodes, ablation elements (e.g., ablation tip electrodes for delivering RF ablative energy, high intensity focused ultrasound ablation elements, etc.), and corresponding conductors or leads.

Connector 22 provides mechanical, fluid, and electrical connection(s) for cables, such as, for example, cables 34, 36 extending to model construction system 14 and/or other components of system 10 (e.g., a visualization, navigation, and/or mapping system (if separate and distinct from model construction system 14), an ablation generator, irrigation source, etc.). Connector 22 is conventional in the art and is disposed at a proximal end of catheter 12, and handle 24 thereof, in particular.

Handle 24, which is disposed at proximal end 28 of shaft 26, provides a location for the clinician to hold catheter 12 and may further provide means for steering or guiding shaft 26 within body 18 of the patient. For example, handle 24 may include means to change the length of a steering wire extending through catheter 12 to distal end 30 of shaft 26 to steer shaft 26. Handle 24 is also conventional in the art and it will be understood that the construction of handle 24 may vary. In other embodiments, catheter 12 may be robotically driven or controlled. Accordingly, rather than a clinician manipulating a handle to steer or guide catheter 12 and shaft 26 thereof, in such an embodiments, a robot is used to manipulate catheter 12.

Shaft 26 is an elongate, tubular, flexible member configured for movement within body 18. Shaft 26 supports, for example and without limitation, sensors and/or electrodes mounted thereon, such as, for example, sensors 32, associated conductors, and possibly additional electronics used for signal processing and conditioning. Shaft 26 may also permit transport, delivery, and/or removal of fluids (including irrigation fluids, cryogenic ablation fluids, and bodily fluids), medicines, and/or surgical tools or instruments. Shaft 26 may be made from conventional materials such as polyurethane, and defines one or more lumens configured to house and/or transport electrical conductors, fluids, or surgical tools. Shaft 26 may be introduced into a blood vessel or other structure within the body 18 through a conventional introducer. Shaft 26 may then be steered or guided through body 18 to a desired location, such as heart 20, using means well known in the art.

Sensors 32 mounted in or on shaft 26 of catheter 12 may be provided for a variety of diagnostic and therapeutic purposes including, for example and without limitation, electrophysiological studies, pacing, cardiac mapping, and ablation. In this embodiment, one or more of sensors 32 are provided to perform a location or position sensing function. More particularly, and as will be described in greater detail below, one or more of sensors 32 are configured to be a positioning sensor(s) that provides information relating to the location (position and orientation) of catheter 12, and distal end 30 of shaft 26 thereof, in particular, at certain points in time. Accordingly, as catheter 12 is moved along a surface of a structure of interest of heart 20 and/or about the interior of the structure, sensor(s) 32 can be used to collect location data points that correspond to the surface of, and/or other locations within, the structure of interest. These location data points can then be used by, for example, model construction system 14, in the construction of a three-dimensional model of the structure of interest, which will be described in greater detail below. For purposes of clarity and illustration, the description below will discuss an embodiment wherein multiple sensors 32 of catheter 12 comprise positioning sensors. It will be appreciated, however, that in other embodiments, which remain within the spirit and scope of the present disclosure, catheter 12 may comprise both one or more positioning sensors as well as other sensors configured to perform other diagnostic and/or therapeutic functions.

In addition to performing the position sensing function described above, or in the alternative, one or more of sensors 32 may be configured to measure one or more EP parameters corresponding to the cardiac structure using techniques that are well known in the art. More particularly, as a sensor 32 that is configured to make such measurements is moved along the surface of the cardiac structure, sensor 32 is configured to make measurements of an EP parameter of interest and to communicate the measured value(s) of the parameter to the model construction system 14. The measured value(s) of the EP parameter can then be used by, for example, the model construction system 14, in the construction of an EP map of the cardiac structure on a geometry surface model of the cardiac structure.

While in an exemplary embodiment the position sensing function and EP parameter measurement functions may be performed by different sensors, for purposes of clarity and illustration, the description below will be limited to an embodiment wherein each of sensors 32 of catheter 12 is configured to perform the position sensing and measurement functions. It will be appreciated, however, that embodiments wherein different sensors are used to perform the different functions remain within the spirit and scope of the present disclosure.

As briefly described above, model construction system 14 is configured to construct a three-dimensional model (also referred to as a geometry surface model) of structures within the heart using, in part, location data collected by catheter 12. More particularly, processing apparatus 16 of model construction system 14 is configured to acquire location data points collected by sensor(s) 32 and to then use those location data points in the construction or generation of a model of the structure(s) to which the location data points correspond. In this embodiment, model construction system 14 acquires the location data points by functioning with sensors 32 to collect location data points. In other embodiments, however, model construction system 14 may simply acquire the location data points from sensors 32 or another component in system 10, such as, for example, a memory or other storage device that is part of model construction system 14 or accessible thereby, without affirmatively taking part in the collection of the location data points. Model construction system 14 is configured to construct a three-dimensional model based on some or all of the collected location data points. For purposes of illustration and clarity, the description below will be limited to an embodiment wherein model construction system 14 is configured to both construct the model and also acquire location data points by functioning with sensor(s) 32 in the collection of the location data points. It will be appreciated, however, that other embodiments wherein model construction system 14 only acquires location data points from sensor(s) 32 or another component of system 10 and then constructs a three-dimensional model based thereon remain within the spirit and scope of the present disclosure.

Further, in an exemplary embodiment, processing apparatus 16 is configured to use EP data/information collected by the catheter 12 to modify the three-dimensional model and generate a 3D map.

In some embodiments, system 10 may include an electrical field- and magnetic field-based system such as the ENSITE PRECISION™ system commercially available from Abbott Laboratories, and generally shown with reference to U.S. Pat. No. 7,263,397 entitled "Method and Apparatus for Catheter Navigation and Location and Mapping in the Heart", the entire disclosure of which is incorporated herein by reference. In such embodiments, distal end 30 may include at least one magnetic field sensor—e.g., magnetic coils (not shown). If two or more magnetic field sensors are utilized, a full six-degree-of-freedom registration of magnetic and spatial coordinates could be accomplished without having to determine orthogonal coordinates by solving for a registration transformation from a variety of positions and orientations. Further benefits of such a configuration may include advanced dislodgement detection and deriving dynamic field scaling since they may be self-contained.

In other exemplary embodiments, system 10 may utilize systems other than electric field-based systems. For example, system 10 may include a magnetic field-based system such as the CARTO™ system commercially available from Biosense Webster, and as generally shown with reference to one or more of U.S. Pat. No. 6,498,944 entitled "Intrabody Measurement"; U.S. Pat. No. 6,788,967 entitled "Medical Diagnosis, Treatment and Imaging Systems"; and U.S. Pat. No. 6,690,963 entitled "System and Method for Determining the Location and Orientation of an Invasive Medical Instrument," the disclosures of which are incorporated herein by reference in their entireties.

In yet another exemplary embodiment, system 10 may include a magnetic field-based system such as the GMPS system commercially available from MediGuide Ltd., and as generally shown with reference to one or more of U.S. Pat. No. 6,233,476 entitled "Medical Positioning System"; U.S. Pat. No. 7,197,354 entitled "System for Determining the Position and Orientation of a Catheter"; and U.S. Pat. No. 7,386,339 entitled "Medical Imaging and Navigation System," the disclosures of which are incorporated herein by reference in their entireties.

In a further exemplary embodiment, system 10 may utilize a combination electric field-based and magnetic field-based system as generally shown with reference to U.S. Pat. No. 7,536,218 entitled "Hybrid Magnetic-Based and Impedance Based Position Sensing," the disclosure of which is incorporated herein by reference in its entirety. In yet still other exemplary embodiments, the subsystem 18 may comprise or be used in conjunction with other commonly available systems, such as, for example and without limitation, fluoroscopic, computed tomography (CT), and magnetic resonance imaging (MRI)-based systems.

As briefly described above, sensor(s) 32 of catheter 12 include positioning sensors. Sensor(s) 32 produce signals indicative of catheter location (position and/or orientation) information. Sensor(s) 32 may comprise one or more electrodes and/or one or more magnetic sensors configured to detect one or more characteristics of a low-strength magnetic field. For instance, in one exemplary embodiment, sensor(s) 32 may include magnetic coils disposed on or in shaft 26 of catheter 12.

Figure 2:
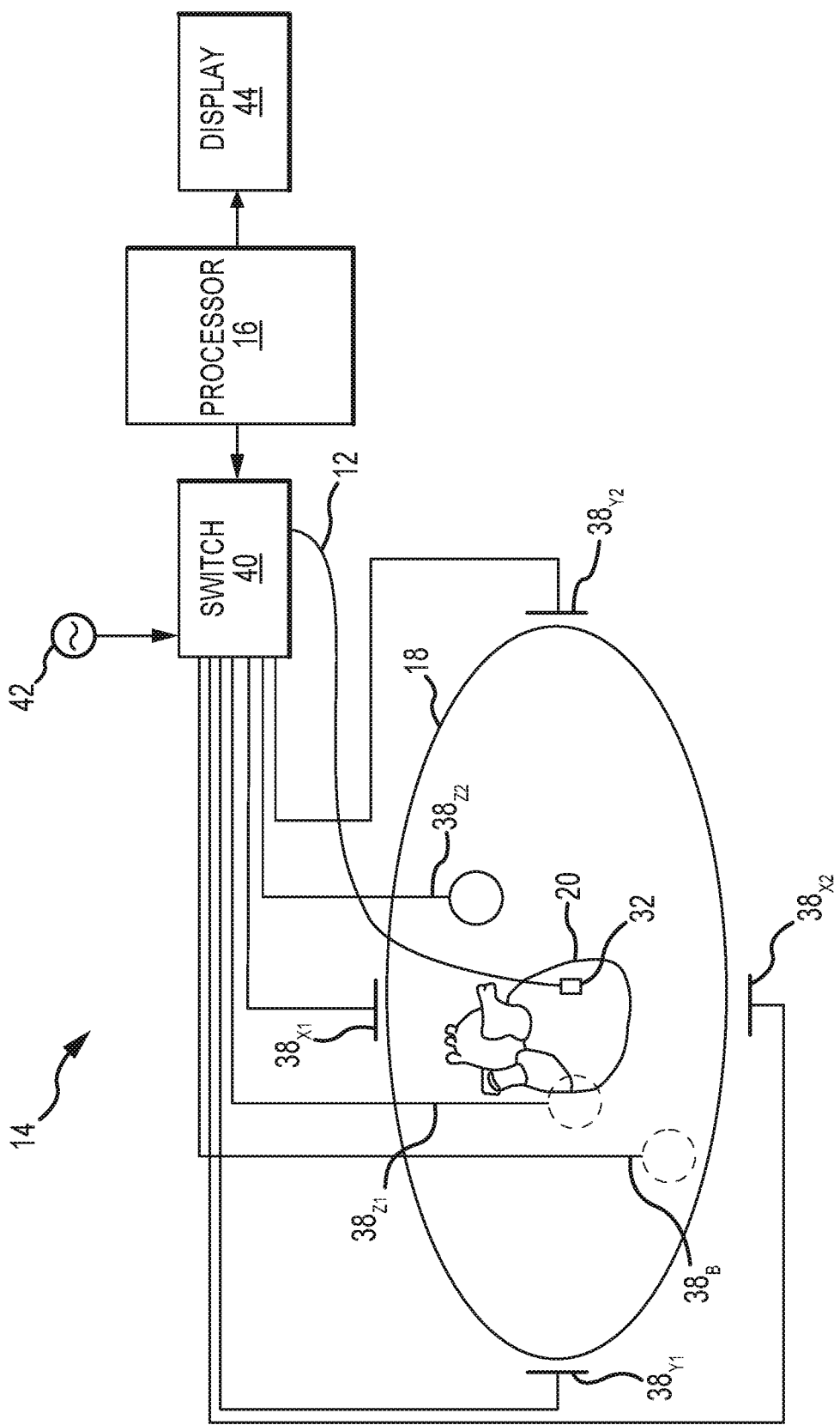
FIG. 2 is a diagrammatic and schematic view of a model construction system of the system illustrated in FIG. 1.

With reference to FIG. 2, in addition to the processing apparatus 16, model construction system 14 may include, among other possible components, a plurality of patch electrodes 38, a multiplex switch 40, a signal generator 42, and a display device 44. In other embodiments, some or all of these components are separate and distinct from model construction system 14 but are electrically connected to, and configured for communication with, model construction system 14.

Processing apparatus 16 may include a programmable microprocessor or microcontroller, or may include an application specific integrated circuit (ASIC). Processing apparatus 16 may include a central processing unit (CPU) and an input/output (I/O) interface through which the processing apparatus 16 may receive a plurality of input signals including, for example, signals generated by patch electrodes 38 and sensor(s) 32, and generate a plurality of output signals including, for example, those used to control and/or provide data to, for example, display device 44 and switch 40. Processing apparatus 16 may be configured to perform various functions, such as those described in greater detail above and below, with appropriate programming instructions or code (i.e., software). Accordingly, processing apparatus 16 is programmed with one or more computer programs encoded on a computer storage medium for performing the functionality described herein.

With the possible exception of patch electrode $38_B$ called a "belly patch," patch electrodes 38 are provided to generate electrical signals used, for example, in determining the position and orientation of catheter 12. In one embodiment, patch electrodes 38 are placed orthogonally on the surface of body 18 and are used to create axes-specific electric fields within body 18. For instance, in one embodiment, patch electrodes $38_{X1}$, $38_{X2}$ may be placed along a first (x) axis.

Patch electrodes $38_{Y1}$, $38_{Y2}$ may be placed along a second (y) axis, and patch electrodes $38_{Z1}$, $38_{Z2}$ may be placed along a third (z) axis. Each of patch electrodes 38 may be coupled to multiplex switch 40. In this embodiment, processing apparatus 16 is configured, through appropriate software, to provide control signals to switch 40 to thereby sequentially couple pairs of electrodes 38 to signal generator 42. Excitation of each pair of electrodes 38 generates an electric field within body 18 and within an area of interest such as heart 20. Voltage levels at non-excited electrodes 38, which are referenced to belly patch $38_B$, are filtered and converted and provided to processing apparatus 16 for use as reference values.

In this embodiment, sensor(s) 32 of catheter 12 are electrically coupled to processing apparatus 16 and are configured to serve a position sensing function. More particularly, sensor(s) 32 are placed within electric fields created in body 18 (e.g., within the heart) by exciting patch electrodes 38. For purposes of clarity and illustration only, the description below will be limited to an embodiment wherein a single sensor 32 is placed within electric fields. It will be appreciated, however, that in other embodiments that remain within the spirit and scope of the present disclosure, a plurality of sensors 32 can be placed within the electric fields and then positions and orientations of each sensor can be determined using the techniques described below.

When disposed within the electric fields, sensor 32 experiences voltages that are dependent on the location between patch electrodes 38 and the position of sensor 32 relative to tissue. Voltage measurement comparisons made between sensor 32 and patch electrodes 38 can be used to determine the location of sensor 32 relative to the tissue. Accordingly, as catheter 12 is swept about or along a particular area or surface of interest, processing apparatus 16 receives signals (location information) from sensor 32 reflecting changes in voltage levels on sensor 32 and from the non-energized patch electrodes 38. Using various known algorithms, the processing apparatus 16 may then determine the location (position and orientation) of sensor 32 and record it as a location data point 46 (also referred to herein as "data point 46" and illustrated in FIG. 3) corresponding to a location of sensor 32, and therefore, a point on the surface or in the interior of the structure of interest being modeled, in a memory or storage device, such as memory 47, associated with or accessible by processing apparatus 16. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Further, locations of other portions of catheter 12 may be interred from measurements at sensors 32, such as by interpolation or extrapolation, to generate further location data points 46. In any event, the collection of location data points 46 ($46_1$, $46_2$, ..., $46_n$) taken over time results in the formation of a point cloud 48 (best shown in FIG. 3) stored in the memory or storage device.

While the description above has thus far been generally with respect to an orthogonal arrangement of patch electrodes 38, the present disclosure is not meant to be so limited. Rather, in other embodiments, non-orthogonal arrangements may be used to determine the location coordinates of sensor 32. For example, and in general terms, FIGS. 4A-4D depict a plurality of exemplary non-orthogonal dipoles $D_0$, $D_1$, $D_2$, and $D_3$, set in a coordinate system 50. In FIGS. 4A-4D, the X-axis patch electrodes are designated $X_A$ and $X_B$, the Y-axis patch electrodes are designated $Y_A$ and $Y_B$, and the Z-axis patch electrodes are designated $Z_A$ and $Z_B$. For any desired axis, the potentials measured across an intra-cardiac sensor, such as sensor 32, resulting from a predetermined set of drive (source sink) configurations may be combined algebraically to yield the same effective potential as would be obtained simply by driving a uniform current along the orthogonal axes. Any two of the patch electrodes $38_{X1}$, $38_{X2}$, $38_{Y1}$, $38_{Y2}$, $38_{Z1}$, and $38_{Z2}$ (See FIG. 2) may be selected as a dipole source and drain with respect to a ground reference, e.g., belly patch $38_B$, while the unexcited patch electrodes measure voltage with respect to the ground reference. Sensor 32 placed in heart 20 is also exposed to the field for a current pulse and is measured with respect to ground (e.g., belly patch $38_B$).

In another exemplary embodiment, multiple patch electrodes 38 may be arranged linearly along a common axis. In such an embodiment, excitation of an electrode pair comprising one of patch electrodes 38 and an electrode mounted on catheter 12 generates an electric field. The non-excited patch electrodes 38 may then measure potentials that can be used to determine the position of sensor 32. Accordingly, in such an embodiment, the excitation of multiple electrode pairs comprising different patch electrodes 38 and the catheter-mounted electrode may be used to determine the position of sensor 32.

Data sets from each of patch electrodes 38 and the sensor 32 are all used to determine the location of sensor 32 within heart 20. After the voltage measurements are made, a different pair of patch electrodes 38 is excited by the current source and the voltage measurement process of the remaining patch electrodes 38 and sensor 32 takes place. Once the location of sensor 32 is determined, and as was described above, the location may be recorded as a data point 46 in the same manner described above. In some embodiments, prior to recording the location as a location data point, the raw location data represented by the signals received by processing apparatus 16 may be corrected by processing apparatus 16 to account for respiration, cardiac activity, and other artifacts using known or hereafter developed techniques. Accordingly, it will be appreciated that any number of techniques may be used to determine locations of sensor 32 and to, therefore, collect data points corresponding thereto, each of which remains within the spirit and scope of the present disclosure.

Figure 3:
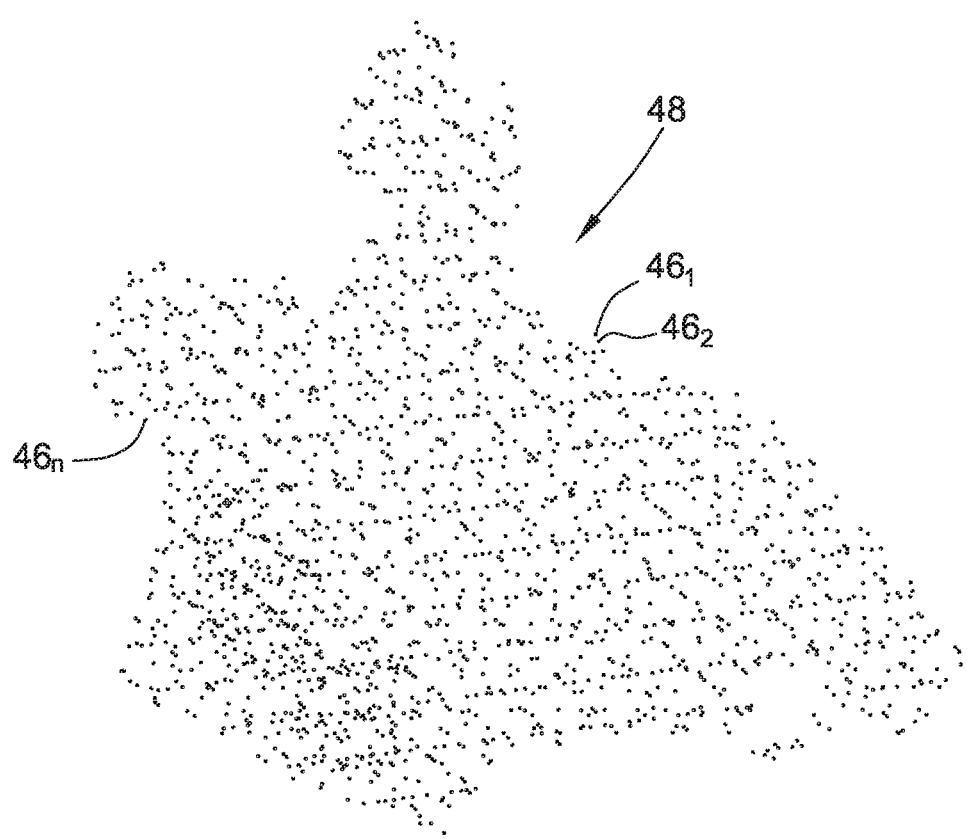
FIG. 3 is a schematic view of a point cloud containing a collection of location data points.
Figure 4A:
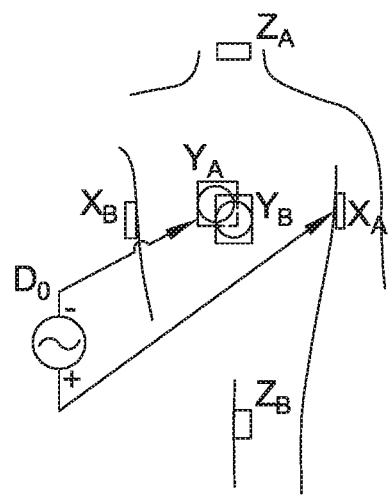
FIGS. 4A-4D are schematic diagrams of exemplary dipole pairs of driven patch electrodes suitable for use in the model construction system illustrated in FIG. 2.
Figure 4B:
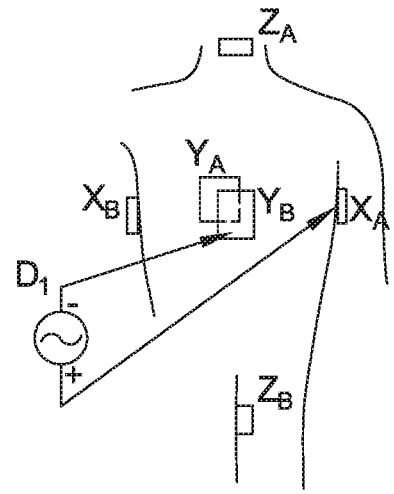
Figure 4C:
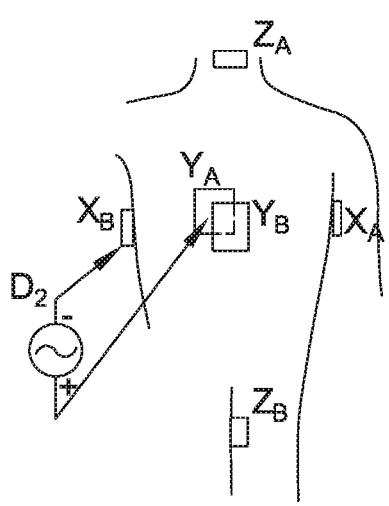
Figure 4D:
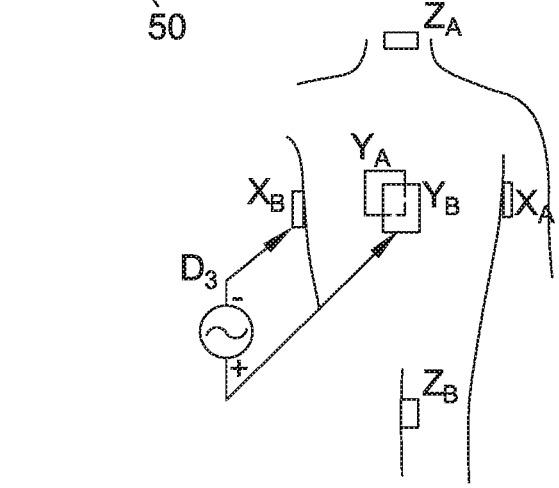

FIG. 3 is illustrative of the point cloud 48 including location data points $46_1$, $46_2$, ... $46_n$ corresponding to a particular structure of interest being modeled. It will be appreciated that in practice, the point cloud 48 would generally include hundreds to hundreds of thousands of data points 46. For purposes of illustration and ease of description, however, the description below will be limited to a point cloud having a limited number of location data points, such as, for example, point cloud 48 including location data points 46. It will be further appreciated that location data points 46 corresponding to different regions of the structure of interest may be collected. In such an embodiment, processing apparatus 16 may be configured to group data points 46 corresponding to the region of the structure of interest from which they were collected. As such, if there are two regions of the structure of interest, all of the location data points corresponding to a first region will be grouped together and form a first point cloud, while all of the data points corresponding to a second region will be likewise grouped together and form a second point cloud.

As described elsewhere herein, processing apparatus 16 is configured to acquire the location data points in a number of ways. In this embodiment, processing apparatus 16 acquires the location data points from sensor 32, which collects the location data points from the surface of the structure. In other embodiments, processing apparatus 16 acquires the sets of location data points by obtaining them from a memory or storage device that is part of or electrically connected to, and configured for communication with, processing apparatus 16. Accordingly, processing apparatus 16 may acquire the sets of location data points (and the location data points thereof) from one of any number of sources, each of which remain within the spirit and scope of the present disclosure. Using the respective sets of location data points 46, processing apparatus 16 is configured to generate surface models of each region of interest.

Once one or more sets of location data points 46 are acquired, processing apparatus 16 is configured to generate a geometry surface model based on the location data points 46. To do so, and in general terms, processing apparatus 16 then uses the acquired one or more sets of location data points 46 to generate the geometry surface model using a surface reconstruction technique, such as an alpha-hull technique.

As described above, in addition to being configured to obtain (e.g., construct or generate, or otherwise acquire) a geometry surface model of the cardiac structure, processing apparatus 16 is further configured to construct an EP map corresponding to the cardiac structure using one or more EP parameters. The EP parameters of the cardiac structure may be, such as, for example and without limitation, those described in great detail in U.S. Pat. No. 7,774,051 entitled "System and Method for Mapping Electrophysiology Information onto Complex Geometry," the entire disclosure of which is incorporated herein by reference. To summarize, however, the EP parameters may include, for example, voltage measurements, peak-to-peak voltage measurements, electrograms, complex fractionated electrograms (CFE), activation direction, and other time- and frequency-domain data. It will be appreciated by those of ordinary skill in the art that a single EP parameter or multiple EP parameters may be measured, and in certain embodiments, used to update the geometry surface model. Accordingly, embodiments wherein more than one EP parameter is measured remain within the spirit and scope of the present disclosure.

To construct the EP map, processing apparatus 16 is configured to first acquire EP data that may be used to calculate the EP parameters (or that may be EP parameters themselves). More particularly, as sensor 32 (or sensors 32, in an embodiment wherein multiple sensors are used) is moved along the surface of the cardiac structure, sensor 32 is configured to make one or more measurements of EP data of interest. In an exemplary embodiment, a measurement of the EP data is made in response to a user command. More particularly, in an exemplary embodiment, system 10 further comprises a user input device 53 (shown in FIG. 1), which may include a touch screen, a keyboard, a keypad, a button, a mouse, a graphical user interface having one or more user-selectable or user-inputtable fields, or some other user-controllable input device that is electrically connected to processing apparatus 16, through which a user may issue a command to make an EP data measurement. Alternatively, processing apparatus 16 may be configured to automatically make such a measurement upon detecting that an event, such as, for example, an activation, has occurred, or otherwise determines or detects that the information relating to the EP parameter being measured is reliable. In any event, by virtue of sensor 32 being electrically connected to processing apparatus 16, once a measurement is made or taken, an electrical signal produced by sensor 32 and representative of the measured value of the EP data is communicated to processing apparatus 16.

Regardless of how a measurement is triggered, each time a measurement is made, processing apparatus 16 is configured to determine the location (position and orientation) of sensor 32 that made the measurement. The location is recorded as a measurement point in a memory or storage device associated with, or accessible by, processing apparatus 16, such as, for example, memory 47. Each measurement point is also associated and recorded with the measured EP data value that corresponds to that particular measurement point. In an exemplary embodiment, processing apparatus 16 is configured to determine the location of sensor 32, and therefore, the corresponding measurement point, in the same manner as that described above with respect to the determination of the location of sensor 32 and the corresponding location data point 46. As such, the description set forth above applies here with equal weight and will not be repeated, rather it is incorporated here by reference. The collection of measurement points taken over time results in a formation of a point cloud stored in a memory or storage device (such as memory 47), which, along with the EP data values corresponding to each measurement point 46, may be used by the processing apparatus 16 to update the geometry surface model and construct the EP map.

To construct the 3D map, in some embodiments, EP parameters are calculated and overlaid onto the geometry surface model to generate an EP map. For example, the EP parameters may be represented using colors, symbols, etc. There may be uncertainties in those EP parameters, and, as a result, it would be advantageous (e.g., to physicians) to indicate how likely it is that a particular EP parameter is reliable. Accordingly, the systems and methods disclosed herein describe calculating confidence metrics for EP parameters and adjusting a displayed EP map based on those confidence metrics. The confidence metric, in at least some embodiments, represents the predicted probability, given observed factors, that an expert observer would assign a high confidence in the reliability of the particular EP parameter.

Activation direction for omnipolar mapping is one example EP parameter that a confidence metric may be calculated for. Calculating confidence metrics for activation direction values is useful, as the reliability of a given activation direction may be relatively difficult to assess in vivo, due to the absence of ground truth. Further, determined activation directions are susceptible to being unreliable, as noise artifacts and physiological complexity can negatively impact activation direction calculations. Although the examples and embodiments described herein are directed to activation direction, those of skill in the art will appreciate that confidence metrics may be similarly calculated for other EP parameters.

Figure 5:
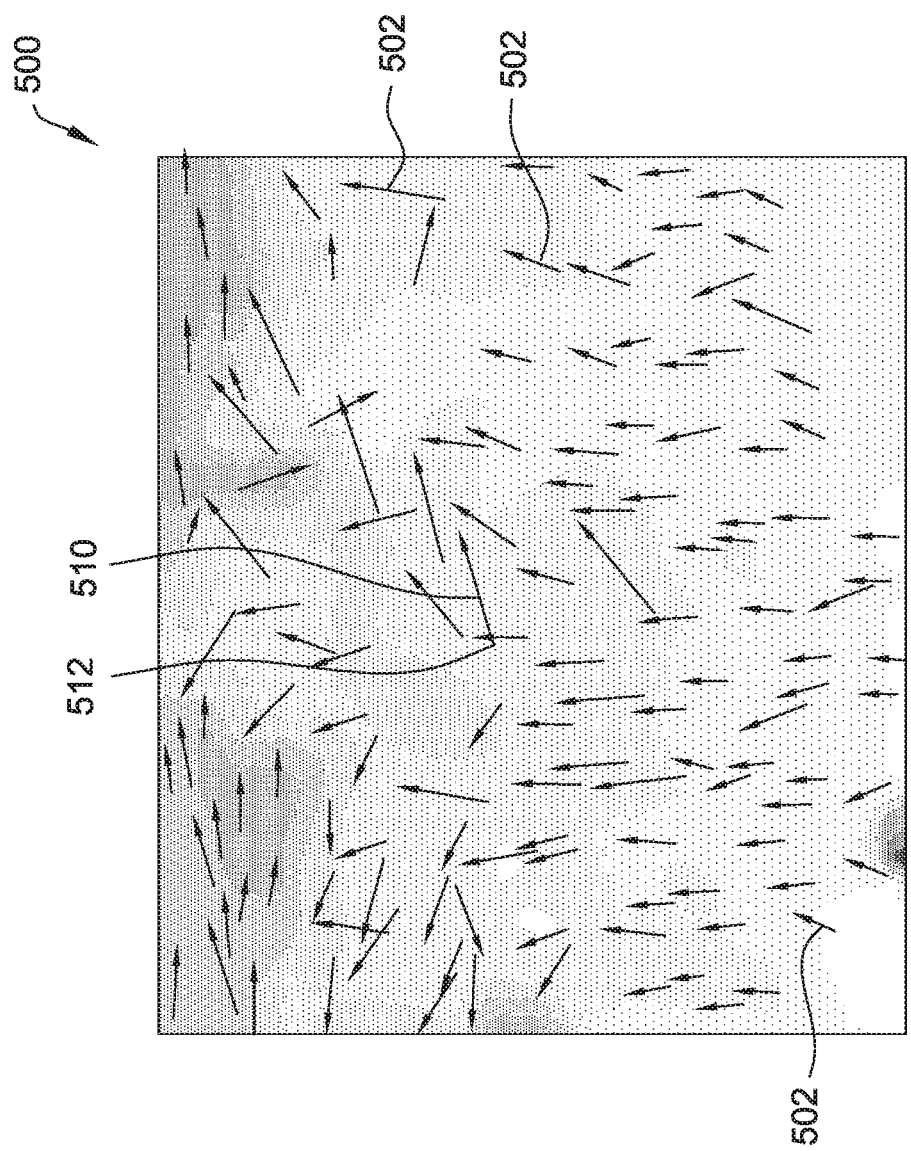
FIG. 5 is a portion of an example EP map including displayed EP parameters.

The activation direction at a given point on the geometry surface model is the direction that electrical waves propagate along when passing through that point. The activation direction may be calculated, for example, by matching spatial and temporal derivatives for the point. The activation direction, in some embodiments, is represented by an arrow on the displayed EP map. For example FIG. 5 illustrates a portion of an example EP map 500 that includes a plurality of EP parameters 502. In this embodiment, EP parameters 502 are arrows indicating an activation direction. Alternatively, those of skill in the art will appreciate that other EP parameter indicators may be displayed (e.g., using colors, symbols, animated depictions, etc.).

As shown in FIG. 5, EP parameters 502 collectively illustrate the general propagation pattern of electrical waves. However, at least some individual EP parameters 502 appear to contradict the overall pattern, and thus could be interpreted (e.g., by a clinician) as being unreliable, even if the indicators are ultimately physiologically correct (e.g., at breakout sites, wavefront collision sites, or at ablation lesion sites). For example, a first EP parameter 510 appears to be inconsistent with a second EP parameter 512 that is nearby. Accordingly, the systems and methods described herein enable generating confidence metrics for EP parameters (such as activation direction) and updating the displayed EP map based on the generated confidence metrics, as described herein.

Figure 6:
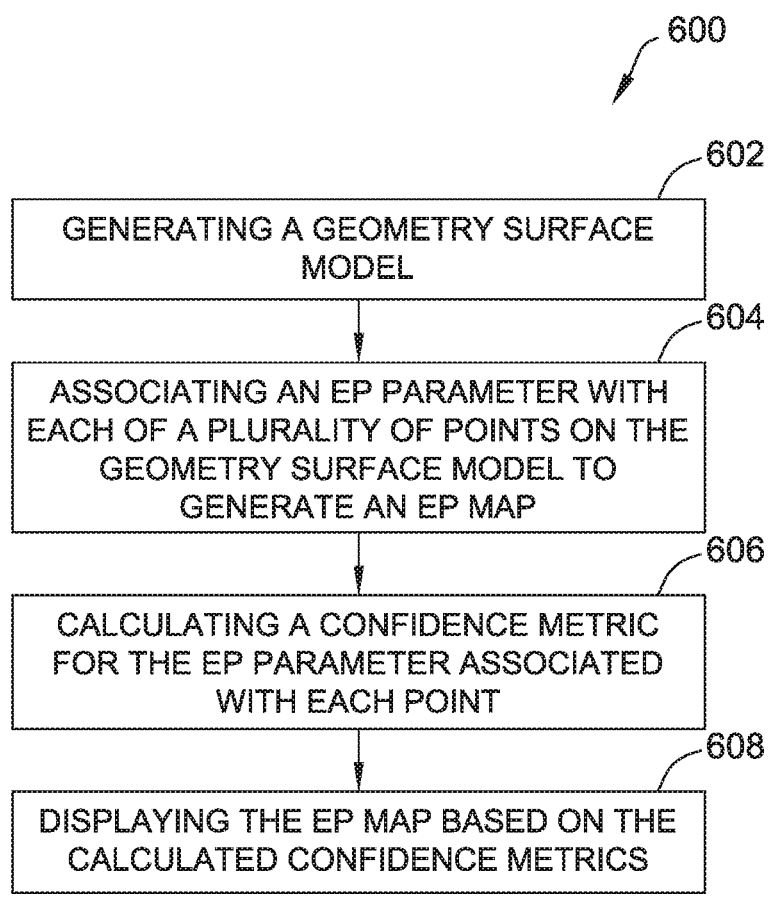
FIG. 6 is a flow diagram of one embodiment of a method for generating and displaying an EP map.

FIG. 6 is a flow diagram of one embodiment of a method 600 for generating and displaying an EP map. Method 600 may be implemented, for example, using model construction system 14 (shown in FIG. 1). Method 600 includes generating 602 a geometry surface model. The geometry surface model may be generated 602, for example, using one or more techniques described herein. Alternatively, the geometry surface model may be generated 602 using any suitable technique.

Method 600 further includes associating 604 an EP parameter with each of a plurality of points on the geometry surface model to generate an EP map. The EP parameter may be, for example, activation direction. In addition, method 600 includes calculating 606 a confidence metric for the EP parameter associated with each point. The confidence metric may be calculated 606 as described in detail below. Further, method 600 includes displaying 608 the EP map based on the calculated confidence metrics. The EP map may be displayed 608, for example, as described in detail below.

In the systems and methods described herein, confidence metrics may be calculated as follows. Specifically, in some embodiments, the confidence metric for a given EP parameter is calculated as a value between a lower bound (e.g., 0) and an upper bound (e.g., 1), where a confidence value at the upper bound indicates the associated EP parameter has a 100% probability of being reliable, and where a confidence value at the lower bound indicates the associated EP parameter has a 0% probability of being reliable. As will be appreciated by those of skill in the art, other scales/values may be used for the confidence metric without departing from the spirit and scope of the disclosure.

In some embodiments, confidence metrics may be calculated based on one or more confidence predictors that may be indicative of the reliability of an EP parameter of interest (e.g., activation direction). These confidence predictors may be identified using the following methodologies. First, one or more expert observers (e.g., clinicians) review a plurality of previously generated EP maps including multiple instances of the EP parameter of interest (each associated with a respective point). In this embodiment, the expert observers review the previously generated maps, and indicate, for each point, a confidence assessment for the associated EP parameter. The confidence assessment may, for example, indicate whether the expert observer has a high confidence or low confidence that the EP parameter associated with the particular point is reliable. The confidence assessments may be assigned based on, for example, consistency with adjacent values, conformity with physiology, and agreement with local activation time (LAT) isochrones. Alternatively, special instrumentation (e.g., in addition to or as an alternative to expert observer assessments) that is impractical for routine clinical applications may be used to assess map point confidence with certainty.

Then, for each map point assessed by the expert observers and/or special instrumentation, a plurality of indices associated with that point are recorded. The indices may include, for example, assessments of voltage amplitude such as peak-to-peak omnipole voltage, maximum bipole peak-to-peak voltage, minimum bipole peak-to-peak voltage; electrogram signal complexity; interrelated indices of signal temporal and spatial extent including wave duration, wave extent, and conduction velocity; omnipole related indices that assess similarity to a traveling wave of depolarization including waveform, correlation coefficient, voltage loop eccentricity, degree of variation in unipolar amplitudes, temporal disparities between unipolar depolarizations, directional disparity between maximal bipole voltage axis and activation direction; departures of waveform morphology from idealized traveling wave waveforms; proximity of mapping electrodes to the cardiac surface; velocity of the mapping catheter over the cardiac surface; etc.

Referring to the above indices in more detail, peak-to-peak quantification of an ordinary voltage signal is defined as the difference between maximum and minimum voltage values over some predetermined period of time. The omnipolar treatment of peak-to-peak amplitude extends to the span of two- or three-dimensional voltage loops over a similar interval of depolarization and possible directions. Electrogram signal complexity may be quantified by the number of zero crossings of a suitably filtered signal over a specified time interval to thereby measure the degree of fractionation or number of discrete depolarizations in close succession. Spatial and temporal extents of a depolarization wave may be assessed by, for example, determining the distance in the direction of activation of simultaneous electrical activity and duration of activity at an electrode's location. For a traveling wave they are related by conduction velocity speed such that wave spatial extent is equal to conduction speed multiplied by wave duration.

The depolarization wavefronts most reliably characterized are those that resemble traveling waves that locally possess a nearly constant direction, speed, amplitude, and shape. As will be appreciated by those of skill in the art, the spatial and temporal derivatives of traveling waves should closely resemble each other except for amplitude. Therefore, another index of confidence in derived quantities is the correlation coefficient between the bipolar voltage in the direction of activation and the time derivative of unipolar voltage. Ideal depolarization waves possess a single direction which manifests as an exceptionally thin voltage loop. An index of eccentricity is the ratio of the loop's maximal span to its minimal span. As mentioned previously, a traveling wave's nearby unipolar electrograms should have very similar amplitudes. One practical index of similarity is thus the coefficient of variation of unipolar amplitudes. A traveling wave of physiologic origin must have a conduction velocity within biophysical limits. As a result, the temporal disparity (for a fixed interelectrode spacing) between its local unipolar waveforms should neither be too small (implying its speed is too great) or too large (implying speed is too slow).

One measure of temporal disparity is the greatest pairwise time difference between nearby unipolar electrodes. In the absence of substantial wavefront curvature or variation in conduction speed, the directions of the maximal bipole axes and activation directions should be very similar. A measure of directional disparity is thus the angle between them, which is constrained to be between 0 and 90 degrees. Another index that reflects consistent speed and direction of activation is the dispersion of an EP parameter, such as activation direction, in a region about a map point. Lastly, the orderly sequence of ion currents that result in the spread of myocardial activation imposes restrictions on possible electrogram waveforms. One technique to quantify conformity to possible waveforms is to track the maximum correlation coefficient between observed waveforms and a collection of template waveforms that model possible signals.

Based on the plurality of confidence assessments and the indices associated with each confidence assessment, mathematical expressions linking confidence assessments and indices can be obtained. It is notable that confidence assessments derived for one EP parameter are often similar to those for other EP parameters. That is, one can not only determine which indices (referred to herein as 'predictive indices') for a point can be used to predict whether an EP parameter should have a high confidence or a low confidence assessment, but also this confidence assessment may be applicable to multiple EP parameters.

In some embodiments, the indices (including various powers of the indices and combinations of indices) may be analyzed using receiver operating characteristic (ROC) curves and regressions (e.g., binary logistic regressions) to identify the strongest candidates for predictive indices. Then, the predictive indices are used to automatically generate a model that can be used to calculate a confidence metric for EP parameters that reasonably replicates the confidence assessment that would be assigned by an expert observer.

For example, from the plurality of confidence assessments and the indices associated with each confidence assessment, suppose that eccentricity is an index recorded for each point, and suppose that voltage loop eccentricity is believed to be one of several valuable predictive indices (i.e., the confidence assessment may be tied to eccentricity and other values). Then, using a logistic regression, a model is generated that expresses the confidence metric as a function of a subset of the predictive indices (in this example only eccentricity). Subsequently, suppose an EP parameter is associated with a first point, and an eccentricity value is also recorded for the first point during an EP study. Using the previously generated model, a confidence metric for the EP parameter can be calculated based on the eccentricity value. Those of skill in the art will appreciate that confidence metrics for EP parameters associated with other points would be calculated similarly.

In some embodiments, one or more transformations are performed on the indices before they are analyzed to identify predictive indices and generate the model. For example, eccentricity, as defined earlier, takes on values from 1 to infinity, which results in large values of eccentricity dominating at the expense of other indices. Accordingly, eccentricity may be transformed by analyzing 1/eccentricity (which ranges from 0 to 1) instead. Other indices (e.g., conduction velocity) may also be transformed prior to analysis.

Once a confidence metric is calculated for the EP parameter associated with each point (e.g., at 606 in FIG. 6), the EP map may be displayed based on the calculated confidence metrics (e.g., at 608), as described herein. The following are multiple examples of displaying an EP map based on confidence metrics. However, those of skill in the art will appreciate that other techniques for displaying EP maps, although not specifically described herein, are within the spirit and scope of the disclosure.

Figure 7A:
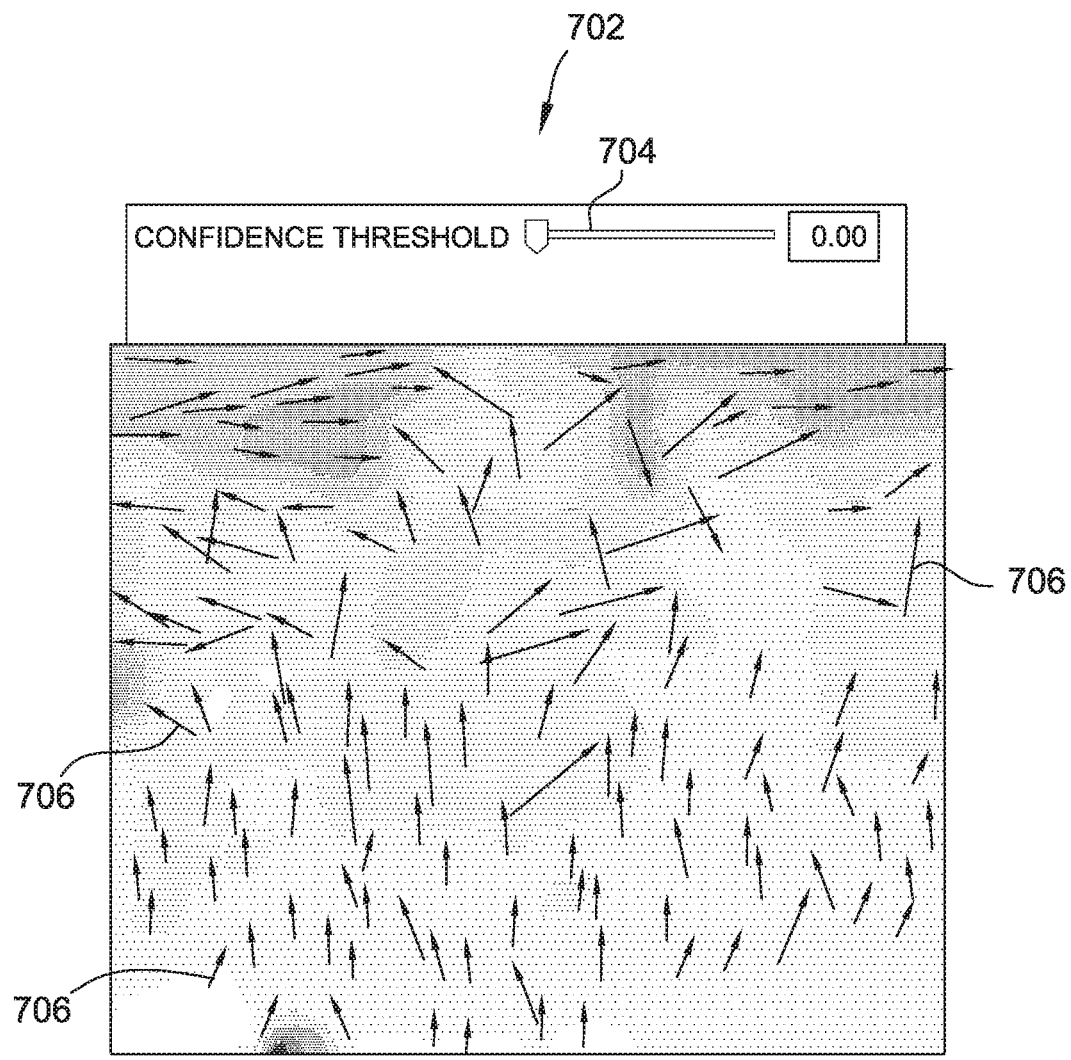
FIGS. 7A and 7B are portions of an EP map that are displayed based on calculated confidence metrics.
Figure 7B:
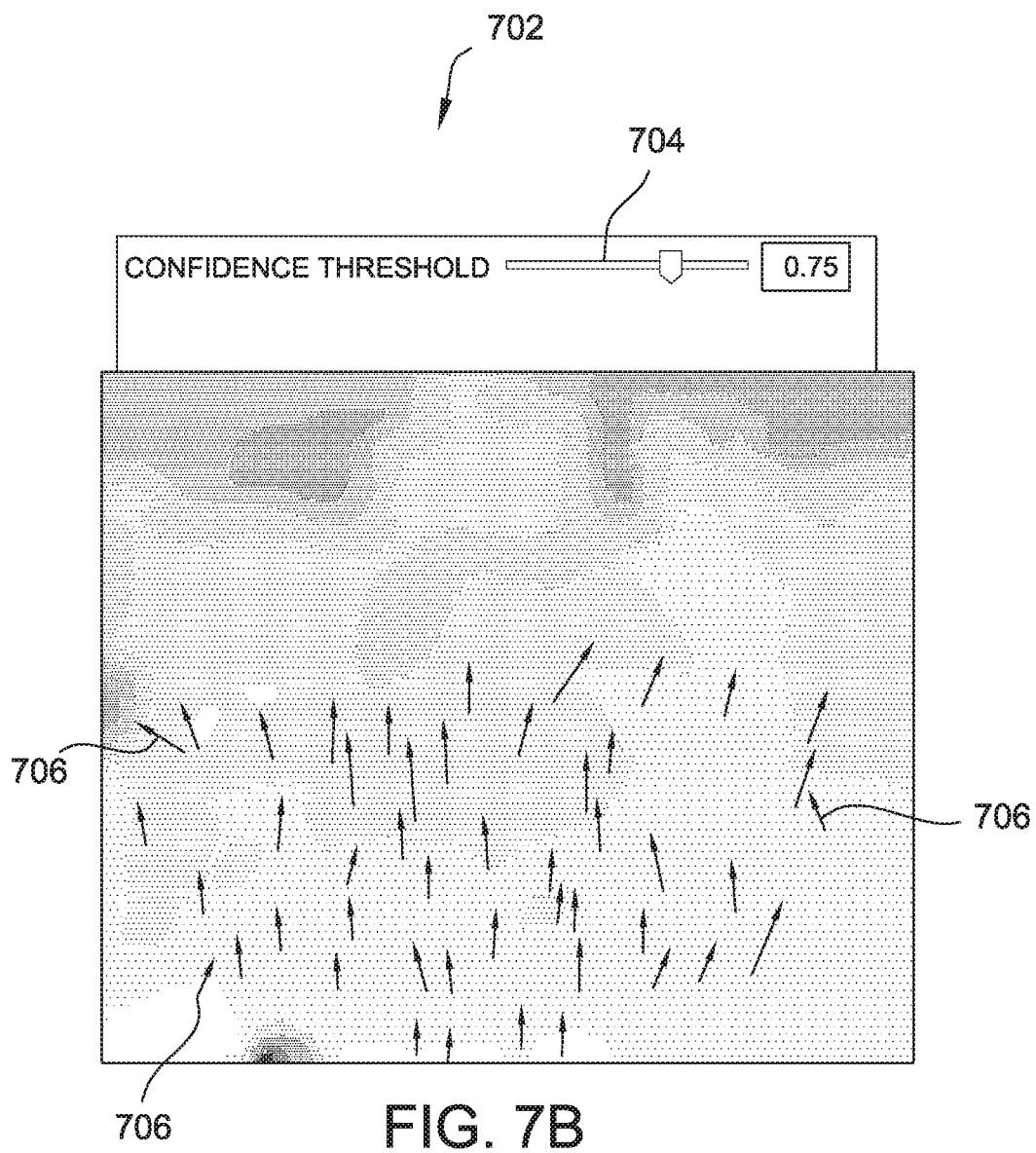

As shown in FIGS. 7A and 7B, in one example, a portion of an EP map 702 is displayed on a display device (e.g., display device 44 shown in FIG. 1) in association with a confidence threshold slider 704. Confidence threshold slider 704 may be manipulated by a user (e.g., using user input device 53 shown in FIG. 1).

In this embodiment, confidence threshold slider 704 sets a threshold (e.g., on a scale from 0 to 1) that determines which EP parameters are shown on the EP map. Specifically, each EP parameter has an associated confidence value between 0 and 1, and only those EP parameters with a confidence value greater than the selected threshold are displayed on the EP map. For example, if confidence threshold slider 704 is set at a threshold of 0 (as shown in FIG. 7A), all of the EP parameters will be displayed, because all of the EP parameters have a calculated confidence value greater than or equal to 0. In contrast, if confidence threshold slider 704 is set at a threshold of 1, none of the EP parameters will be displayed, because all of the EP parameters have a calculated confidence value less than 1. Further, if the confidence threshold slider 704 is set at a threshold somewhere between 0 and 1 (as shown in FIG. 7B), only some of the EP parameters may be displayed (depending on the calculated confidence values).

In this way, confidence threshold slider 704 allows a user to control the likely reliability of the information displayed. For example, if the user is only interested in viewing EP parameters that are very likely to be correct, the user can set confidence threshold slider 704 relatively close to 1. Alternatively, if the user is interested in seeing more information, with the understanding that the information may be less reliable, the user may set confidence threshold slider 704 lower. Further, if the user sets the confidence threshold slider 704 relatively close to 1, and relatively few EP parameters are shown, the user may elect to collect additional EP information (e.g., using catheter 12 shown in FIG. 1), perhaps correcting for artifacts or poor initial contact with myocardial tissue.

In an alternative embodiment, only EP parameters with a confidence value less than the selected threshold of confidence threshold slider 704 are displayed. This may be beneficial, as regions of low confidence may be concentrated in pathologic areas that may initiate or sustain arrhythmias. Concentrating a display of map points in these regions may be a valuable guide to a clinician deciding where to deliver ablation therapy.

Referring now to FIGS. 7A and 7B in particular, FIG. 7A shows confidence threshold slider 704 set at a threshold of 0. Accordingly, all of the activation direction indicators 706 are shown for EP map 702. In contrast, in FIG. 7B, confidence threshold slider 704 is set at a threshold of 0.75. Accordingly, only activation direction indicators 706 that have a relatively high calculated confidence metric (i.e., greater than or equal to 0.75) are shown.

In another example, the EP map may be initially displayed with the threshold set at 0, and the threshold may gradually and automatically increase over a predetermined period of time (e.g., 30 seconds) until the threshold reaches 1. In this example, all of the EP parameters will be initially displayed, and as the threshold increases automatically, EP parameters with lower confidence thresholds will be removed from the displayed EP map.

In another example, the EP map may be initially displayed with the threshold set at 1, and the threshold may gradually and automatically decrease over a predetermined period of time (e.g., 30 seconds) until the threshold reaches 0. In this example, none of the EP parameters will be initially displayed, and as the threshold decreases automatically, EP parameters with higher confidence metrics will appear prior to EP parameters with lower confidence metrics.

The calculated confidence metrics may also be utilized in other manners to affect the display of the EP map (including the acquisition of the EP map). For example, in some embodiments, if a first EP parameter and a second EP parameter are both associated with a single point, the confidence metrics for each EP parameter may be used to select a final EP parameter for that point (i.e., by selecting the EP parameter with the higher confidence metric). In another example, if a first EP parameter is stored in association with a point at a first time, and a second EP parameter is determined for a second point so close to the first point as to be practically indistinguishable at a second time (e.g., due to updated EP measurements), the first EP parameter may be replaced with the second EP parameter if the confidence metric for the second EP parameter is higher than the confidence metric for the first EP parameter. In yet another example, only EP parameters with a confidence metric above a predetermined threshold are stored in association with points (e.g., EP parameters with a confidence metric below the predetermined threshold are discarded). In yet another example, a map of confidence itself may be valuable to delimit health from diseased tissue areas where therapies may be directed. In yet another example, the confidence values of nearby points may be used to generate additional map point results (e.g., EP parameters) that reflect a weighted average of nearby results. Those of skill in the art will appreciate that the EP map may be displayed based on the calculated confidence metrics using other suitable techniques as well.

The systems and methods described herein are directed to displaying an electrophysiology (EP) map are provided. Initially, a plurality of location data points are collected, and a geometry surface model is generated from the set of location data points. To generate an EP map, an EP parameter is associated with each of a plurality of points on the geometry surface model. A confidence metric is calculated for each EP parameter, and the EP map is displayed based on the calculated confidence metrics.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. A system for generating and displaying an electrophysiology (EP) map, the system comprising:
   a catheter comprising at least one positioning sensor configured to:
   collect a set of location data points while the catheter is maneuvered within a subject; and
   a computer-based model construction system coupled to the catheter and configured to:
   generate a geometry surface model from the set of location data points;
   associate an EP parameter with each of a plurality of points on the geometry surface model to generate an EP map;
   calculate a confidence metric for the EP parameter associated with each point, wherein the confidence metric represents a predicted probability that a clinician would find that EP parameter to be reliable, and wherein to calculate the confidence metric, the computer-based model construction system is configured to:
   obtain, for each of a plurality of points on each of a plurality of previously generated EP maps, a confidence assessment for the EP parameter, the confidence assessments made by one or more clinicians;
   obtain a plurality of indices for each of the plurality of points on each of the plurality of previously generated EP maps; and
   calculate the confidence metric based on the confidence assessments and the plurality of indices; and
   display the EP map based on the calculated confidence metrics.

2. The system of claim 1, wherein to associate an EP parameter with each of a plurality of points, the computer-based model construction system is configured to associate an activation direction with each of the plurality of points.

3. The system of claim 1, wherein to calculate a confidence metric, the computer-based model construction system is configured to calculate a confidence metric between a lower bound and an upper bound.

4. The system of claim 3, wherein the lower bound is 0 and the upper bound is 1.

5. The system of claim 3, wherein to display the EP map, the computer-based model construction system is configured to:
   display a slider that enables a user to set a threshold between the upper bound and the lower bound; and
   display only EP parameters that have a calculated confidence metric greater than or equal to the threshold.

6. The system of claim 5, wherein to display the EP map, the computer-based model construction system is configured to:
   initially set the threshold to the lower bound such that all of the EP parameters are displayed; and
   gradually increase the threshold to the upper bound over a predetermined period of time.

7. The system of claim 5, wherein to display the EP map, the computer-based model construction system is configured to:
  initially set the threshold to the upper bound such that none of the EP parameters are displayed; and
  gradually decrease the threshold to the lower bound over a predetermined period of time.

8. The system of claim 1, wherein to calculate the confidence metric based on the confidence assessments and the plurality of indices, the computer-based model construction system is configured to:
  obtain mathematical expressions linking the confidence assessments and the plurality of indices;
  generate a model based on the mathematical expressions; and
  calculate the confidence metric using the generated model.

9. A computer-implemented method for generating and displaying an electrophysiology (EP) map, the method comprising:
  receiving, from a catheter including at least one positioning sensor, a set of location data points acquired using the at least one positioning sensor while the catheter is maneuvered within a subject;
  generating a geometry surface model from the set of location data points;
  associating an EP parameter with each of a plurality of points on the geometry surface model to generate an EP map;
  calculating a confidence metric for the EP parameter associated with each point, wherein the confidence metric represents a predicted probability that a clinician would find that EP parameter to be reliable, and wherein the confidence metric is calculated by:
    obtaining, for each of a plurality of points on each of a plurality of previously generated EP maps, a confidence assessment for the EP parameter, the confidence assessments made by one or more clinicians;
    obtaining a plurality of indices for each of the plurality of points on each of the plurality of previously generated EP maps; and
    calculating the confidence metric based on the confidence assessments and the plurality of indices; and
  displaying the EP map based on the calculated confidence metrics.

10. The method of claim 9, wherein associating an EP parameter with each of a plurality of points comprises associating an activation direction with each of the plurality of points.

11. The method of claim 9, wherein calculating a confidence metric comprises calculating a confidence metric between a lower bound and an upper bound.

12. The method of claim 11, wherein the lower bound is 0 and the upper bound is 1.

13. The method of claim 11, wherein displaying the EP map comprises:
  displaying a slider that enables a user to set a threshold between the upper bound and the lower bound; and
  displaying only EP parameters that have a calculated confidence metric greater than or equal to the threshold.

14. The method of claim 13, wherein displaying the EP map further comprises:
  initially setting the threshold to the lower bound such that all of the EP parameters are displayed; and
  gradually increasing the threshold to the upper bound over a predetermined period of time.

15. The method of claim 13, wherein displaying the EP map further comprises:
  initially setting the threshold to the upper bound such that none of the EP parameters are displayed; and
  gradually decreasing the threshold to the lower bound over a predetermined period of time.

16. A processing apparatus for generating and displaying an electrophysiology (EP) map, the processing apparatus configured to:
  receive, from a catheter coupled to the processing apparatus and including at least one positioning sensor, a set of location data points acquired using the at least one positioning sensor while the catheter is maneuvered within a subject;
  generate a geometry surface model from the set of location data points;
  associate an EP parameter with each of a plurality of points on the geometry surface model to generate an EP map;
  calculate a confidence metric for the EP parameter associated with each point, wherein the confidence metric represents a predicted probability that a clinician would find that EP parameter to be reliable, and wherein to calculate the confidence metric, the processing apparatus is configured to:
    obtain, for each of a plurality of points on each of a plurality of previously generated EP maps, a confidence assessment for the EP parameter, the confidence assessments made by one or more clinicians;
    obtain a plurality of indices for each of the plurality of points on each of the plurality of previously generated EP maps; and
    calculate the confidence metric based on the confidence assessments and the plurality of indices; and
  display the EP map based on the calculated confidence metrics.

17. The processing apparatus of claim 16, wherein to associate an EP parameter with each of a plurality of points, the processing apparatus is configured to associate an activation direction with each of the plurality of points.

18. The processing apparatus of claim 16, wherein to calculate a confidence metric, the processing apparatus is configured to calculate a confidence metric between a lower bound and an upper bound.

19. The processing apparatus of claim 18, wherein to display the EP map, the processing apparatus is configured to:
  display a slider that enables a user to set a threshold between the upper bound and the lower bound; and
  display only EP parameters that have a calculated confidence metric greater than or equal to the threshold.

20. The processing apparatus of claim 19, wherein to display the EP map, the processing apparatus is configured to:
  initially set the threshold to the lower bound such that all of the EP parameters are displayed; and
  gradually increase the threshold to the upper bound over a predetermined period of time.

* * * * *